United States Patent
Algawi et al.

(10) Patent No.: US 11,744,601 B2
(45) Date of Patent: Sep. 5, 2023

(54) SINUPLASTY TOOL

(71) Applicant: BIOSENSE WEBSTER (ISRAEL) LTD., Yokneam (IL)

(72) Inventors: Yehuda Algawi, Binyamina (IL); Assaf Govari, Haifa (IL); Andres Claudio Altmann, Haifa (IL); Vadim Gliner, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 273 days.

(21) Appl. No.: 16/943,742

(22) Filed: Jul. 30, 2020

(65) Prior Publication Data
US 2021/0059700 A1 Mar. 4, 2021

Related U.S. Application Data

(60) Provisional application No. 62/893,884, filed on Aug. 30, 2019.

(51) Int. Cl.
*A61B 8/12* (2006.01)
*A61B 17/24* (2006.01)
(Continued)

(52) U.S. Cl.
CPC ........ *A61B 17/24* (2013.01); *A61B 1/000095* (2022.02); *A61B 1/07* (2013.01);
(Continued)

(58) Field of Classification Search
CPC ................ A61B 1/0055; A61B 1/0057; A61B 2017/00309; A61B 2017/00314;
(Continued)

(56) References Cited

U.S. PATENT DOCUMENTS 5,656,011 A 8/1997 Uihlein et al.
10,203,493 B2 * 2/2019 Kirma .................. G02B 13/001
(Continued)

FOREIGN PATENT DOCUMENTS

CH 690088 4/2000

OTHER PUBLICATIONS

International Search Report dated Jan. 15, 2021 from corresponding PCT Patent Application No. PCT/IB2020/058004.

*Primary Examiner* — Deanna K Hall
(74) *Attorney, Agent, or Firm* — Frost Brown Todd LLP

(57) ABSTRACT

A sinuplasty tool, consisting of a handle, and a rigid tube, containing a rigid tube lumen, having a rigid tube distal end and a rigid tube proximal end connected to the handle. The tool also has a resilient tube, containing a resilient tube lumen, having a resilient tube distal end and a resilient tube proximal end fixed to the rigid tube distal end so that the lumens align. The resilient tube has a multiplicity of separated openings partially encircling the resilient tube so as to form ribs in the resilient tube and permitting the resilient tube to bend. The resilient tube distal end may be inserted into a sinus of a living subject. The tool also has a wire, traversing the aligned lumens, connected to the resilient tube distal end and coupled to the handle, so that applying tension to the wire causes the resilient tube to bend.

20 Claims, 11 Drawing Sheets

(51) Int. Cl.
  *A61B 8/08* (2006.01)
  *A61B 6/03* (2006.01)
  *A61M 29/02* (2006.01)
  *A61B 34/20* (2016.01)
  *A61B 1/07* (2006.01)
  *A61B 1/00* (2006.01)
  *A61B 90/30* (2016.01)
  *A61B 17/00* (2006.01)
  *A61B 90/00* (2016.01)

(52) U.S. Cl.
  CPC ............... *A61B 6/032* (2013.01); *A61B 8/12* (2013.01); *A61B 8/483* (2013.01); *A61B 8/5261* (2013.01); *A61B 34/20* (2016.02); *A61M 29/02* (2013.01); *A61B 2017/00296* (2013.01); *A61B 2017/00323* (2013.01); *A61B 2017/00867* (2013.01); *A61B 2034/2051* (2016.02); *A61B 2034/2065* (2016.02); *A61B 2090/306* (2016.02); *A61B 2090/309* (2016.02); *A61B 2090/3784* (2016.02); *A61B 2217/007* (2013.01); *A61M 2210/0681* (2013.01)

(58) Field of Classification Search
  CPC ........... A61B 2017/00323; A61B 8/12; A61M 2210/0681
  See application file for complete search history.

(56) References Cited

U.S. PATENT DOCUMENTS

| | | |
|---|---|---|
| 11,376,401 B2 * | 7/2022 | Matlock ............. A61M 25/0113 |
| 2011/0071349 A1 | 3/2011 | Drontle et al. |
| 2018/0104461 A1 | 4/2018 | Matlock et al. |
| 2019/0015645 A1 | 1/2019 | Matlock et al. |

* cited by examiner

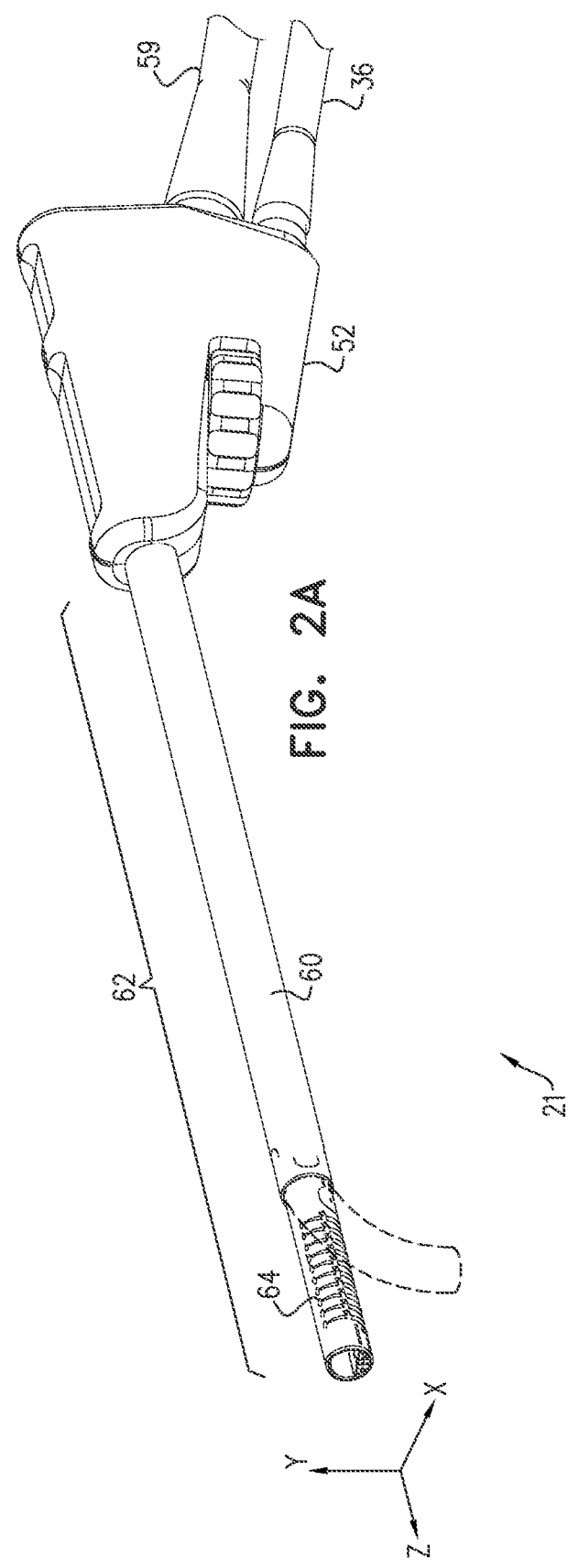

SINUPLASTY TOOL

CROSS-REFERENCE TO RELATED APPLICATIONS

This application claims the benefit of U.S. Provisional Patent Application 62/893,884 filed Aug. 30, 2019, which is incorporated herein by reference.

FIELD OF THE INVENTION

This invention relates generally to surgical tools, and specifically to a surgical tool which may be used for a sinuplasty procedure.

BACKGROUND OF THE INVENTION

Performing a sinuplasty procedure is typically difficult because the sinuses have narrow openings and also vary considerably from person to person. To alleviate the difficulty, a sinuplasty tool should be as narrow and as flexible as possible, while still being rigid enough for a physician to navigate the tool to a desired location.

SUMMARY OF THE INVENTION

An embodiment of the present invention provides a sinuplasty tool, including:

a handle;

a rigid tube, containing a rigid tube lumen, having a rigid tube distal end and a rigid tube proximal end connected to the handle;

a resilient tube, containing a resilient tube lumen, having a resilient tube distal end and a resilient tube proximal end fixedly attached to the rigid tube distal end so that the resilient tube lumen and the rigid tube lumen align, the resilient tube having a multiplicity of separated openings partially encircling the resilient tube so as to form ribs in the resilient tube and permitting the resilient tube to bend, the resilient tube distal end being configured to be inserted into a sinus of a body of a living subject; and a wire, traversing the aligned lumens, connected to a region in proximity to the resilient tube distal end and coupled to the handle, so that applying tension to the wire causes the resilient tube to bend.

In a disclosed embodiment the tool includes locking elements, formed on the ribs, configured to interlock the ribs when the resilient tube is fully bent.

In a further disclosed embodiment the tool includes a resilient strip, fixed to the resilient tube distal end and traversing the aligned lumens. Typically, the wire is looped at, and connected to, a distal end of the resilient strip, the wire having ends connected to a control in the handle. The control may be configured to apply the tension to the wire so as bend the tube, and to release the tension so that the tube returns to an unbent shape.

In a yet further disclosed embodiment a recess is formed in the resilient tube distal end, the recess being formed to facilitate return of a sinuplasty balloon to the tube. A size of the recess may be set in response to a size of the balloon.

In an alternative embodiment the tool includes at least one of a camera, an ultrasound camera, and a fiber optic located in proximity to the resilient tube distal end.

There is further provided, according to an embodiment of the present invention, a method for assembling a tool, including:

forming spring retaining clips in a rigid tube having a rigid tube distal end and a rigid tube proximal end, the rigid tube containing a rigid tube lumen;

cutting apertures configured to mate with the clips in a resilient tube having a resilient tube distal end and a resilient tube proximal end, the resilient tube distal end being configured to be inserted into an orifice of a body of a living subject, the resilient tube containing a resilient tube lumen;

fixedly attaching, by mating the apertures with the clips, the resilient tube proximal end to the rigid tube distal end so that the rigid tube lumen and the resilient tube lumen align;

inserting a resilient strip into the aligned lumens so that a resilient strip distal end aligns with the resilient tube distal end, and fixing the strip distal end to the resilient tube distal end; and connecting a tool handle to the rigid tube proximal end.

In a disclosed embodiment the method includes partially encircling the resilient tube with a multiplicity of openings separating ribs of the resilient tube, the openings permitting the resilient tube to bend. The method may also include forming locking elements on the ribs, the locking elements being configured to interlock the ribs when the resilient tube is fully bent. The method may further include looping a wire at the distal end of the resilient strip, and connecting ends of the wire to a control in the tool handle. The method may yet further include using the control to apply the tension to the wire so as bend the resilient tube, and to release the tension so that the resilient tube returns to an unbent shape.

In a further disclosed embodiment the method includes locating at least one of a camera, an ultrasound camera, and a fiber optic in proximity to the resilient tube distal end.

There is further provided, according to an embodiment of the present invention, a method for analysis of tissue, including:

providing a tool having a camera and a fiber optic end located at a distal end of the tool;

inserting the tool distal end into an orifice of a body of a living subject;

navigating the tool distal end within the body so that an image acquired by the camera includes a region of interest having the tissue;

transmitting analyzing illumination from the fiber optic end to the region of interest;

receiving analyzing illumination reflected from the region of interest via the fiber optic end;

computing a reflectivity of the region of interest in response to the received analyzing illumination; and characterizing the region of interest in response to the reflectivity.

The method may include transmitting visible illumination from the fiber optic end so as to generate the image acquired by the camera.

In a disclosed embodiment characterizing the region of interest includes indicating if the region of interest consists of healthy or diseased tissue.

There is further provided, according to an embodiment of the present invention, a method for generating an enhanced image of tissue, including:

providing a tool having a camera and an ultrasonic camera located at a distal end of the tool;

inserting the tool distal end into an orifice of a body of a living subject;

navigating the tool distal end within the body so that an optical image acquired by the camera includes a region of interest having the tissue;

acquiring a three-dimensional (3D) ultrasound image of the region of interest with the ultrasonic camera;

registering the 3D ultrasound image with the optical image; and combining the registered 3D ultrasound image and optical image to form the enhanced image of the region of interest.

In an alternative embodiment the enhanced image shows a surface of the region of interest derived from the optical image and structure beneath the surface derived from the ultrasound image.

In a further alternative embodiment the method includes registering and combining the enhanced image with a computerized tomography (CT) image having the region of interest so as to form an enhanced CT image, and presenting the enhanced CT image on a screen.

There is further provided, according to an embodiment of the present invention, a method, including:

providing a handle;

connecting to the handle a rigid tube, containing a rigid tube lumen, and having a rigid tube distal end and a rigid tube proximal end;

fixedly attaching a resilient tube, containing a resilient tube lumen and having a resilient tube distal end and a resilient tube proximal end, to the rigid tube distal end so that the resilient tube lumen and the rigid tube lumen align, the resilient tube having a multiplicity of separated openings partially encircling the resilient tube so as to form ribs in the resilient tube and permitting the resilient tube to bend, the resilient tube distal end being configured to be inserted into a sinus of a body of a living subject; and traversing a wire, connected to a region in proximity to the resilient tube distal end and coupled to the handle, through the aligned lumens so that applying tension to the wire causes the resilient tube to bend.

There is further provided, according to an embodiment of the present invention, a sinuplasty tool, including:

a rigid tube having a rigid tube distal end and a rigid tube proximal end, the rigid tube containing a rigid tube lumen;

spring retaining clips formed in the rigid tube;

a resilient tube having a resilient tube distal end and a resilient tube proximal end, the resilient tube distal end being configured to be inserted into an orifice of a body of a living subject, the resilient tube containing a resilient tube lumen;

apertures, cut in the resilient tube, configured to mate with the spring retaining clips so that when the apertures and the clips are mated the resilient tube proximal end fixedly attaches to the rigid tube distal end so that the rigid tube lumen and the resilient tube lumen align;

a resilient strip inserted into the aligned lumens so that a resilient strip distal end aligns with the resilient tube distal end, and so that the resilient strip distal end is fixedly attached to the resilient tube distal end; and a tool handle connected to the rigid tube proximal end.

There is further provided, according to an embodiment of the present invention, apparatus for analysis of tissue, including:

a tool having a camera and a fiber optic end located at a distal end of the tool, the tool distal end being configured to be insertable into an orifice of a body of a living subject; and a processor configured:

to navigate the tool distal end within the body so that an image acquired by the camera includes a region of interest including the tissue, to transmit analyzing illumination from the fiber optic end to the region of interest, to receive analyzing illumination reflected from the region of interest via the fiber optic end, to compute a reflectivity of the region of interest in response to the received analyzing illumination, and to characterize the region of interest in response to the reflectivity.

There is further provided, according to an embodiment of the present invention, apparatus for generating an enhanced image of tissue, including:

a tool having a camera and an ultrasonic camera located at a distal end of the tool, the tool distal end being configured to be inserted into an orifice of a body of a living subject; and a processor, configured:

to navigate the tool distal end within the body so that an optical image acquired by the camera includes a region of interest including the tissue, to acquire a three-dimensional (3D) ultrasound image of the region of interest with the ultrasonic camera, to register the 3D ultrasound image with the optical image, and to combine the registered 3D ultrasound image and optical image to form the enhanced image of the region of interest.

The present disclosure will be more fully understood from the following detailed description of the embodiments thereof, taken together with the drawings, in which:

BRIEF DESCRIPTION OF THE DRAWINGS

FIGS. 2A and 2B are respectively a schematic perspective figure and a schematic cut-away figure of a sinuplasty tool.

DETAILED DESCRIPTION OF EMBODIMENTS

Overview

Embodiments of the present invention provide a multi-purpose sinuplasty tool. In addition to being able to deliver a sinuplasty balloon to a sinus region selected by a physician operating the tool, the tool may also be used to analyze characteristics of tissue in the region, and form an enhanced three-dimensional (3D) image of the region, including structure of the region.

In an embodiment of the present invention the tool has a handle to which is connected a rigid tube. The rigid tube has a rigid tube distal end and a rigid tube proximal end, and it is the proximal end that is connected to the handle. The rigid tube contains a rigid tube lumen.

A resilient tube, typically a super-elastic tube, containing a resilient tube lumen, is fixedly attached by its proximal end to the rigid tube distal end so that the two lumens align. The resilient tube has a multiplicity of separated openings partially encircling the resilient tube so as to form ribs in the resilient tube. The openings permit the resilient tube to bend. The resilient tube distal end is configured to be inserted into a sinus of a body of a living subject.

A wire traverses the aligned lumens The wire is connected to a region in proximity to the resilient tube distal end and is also coupled to the handle, so that applying tension to the wire causes the resilient tube to bend.

In some embodiments a resilient strip is fixed to the resilient tube distal end and traverses the aligned lumens.

In addition to being used for a sinuplasty procedure, the tool typically incorporates fiber optics at the distal end of the resilient tube. The fiber optics can irradiate the sinus region in proximity to the distal tip with visible or near-visible radiation. The fiber optics can also acquire radiation returning from the irradiated region, and a processor can analyze the returned radiation so as to characterize the region.

As a further addition, the tool may be used to form an enhanced image of the sinus region. To form the enhanced image, the tool enables an optical image and an ultrasonic image of the sinus region to be acquired. The optical image is of the surface of the region, while the ultrasonic image is a 3D image showing structure of the region beneath the surface. A processor registers the two images, and the two images in registration, forming an enhanced image of the region, may be presented to a physician using the tool.

DETAILED DESCRIPTION

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Figure 1:
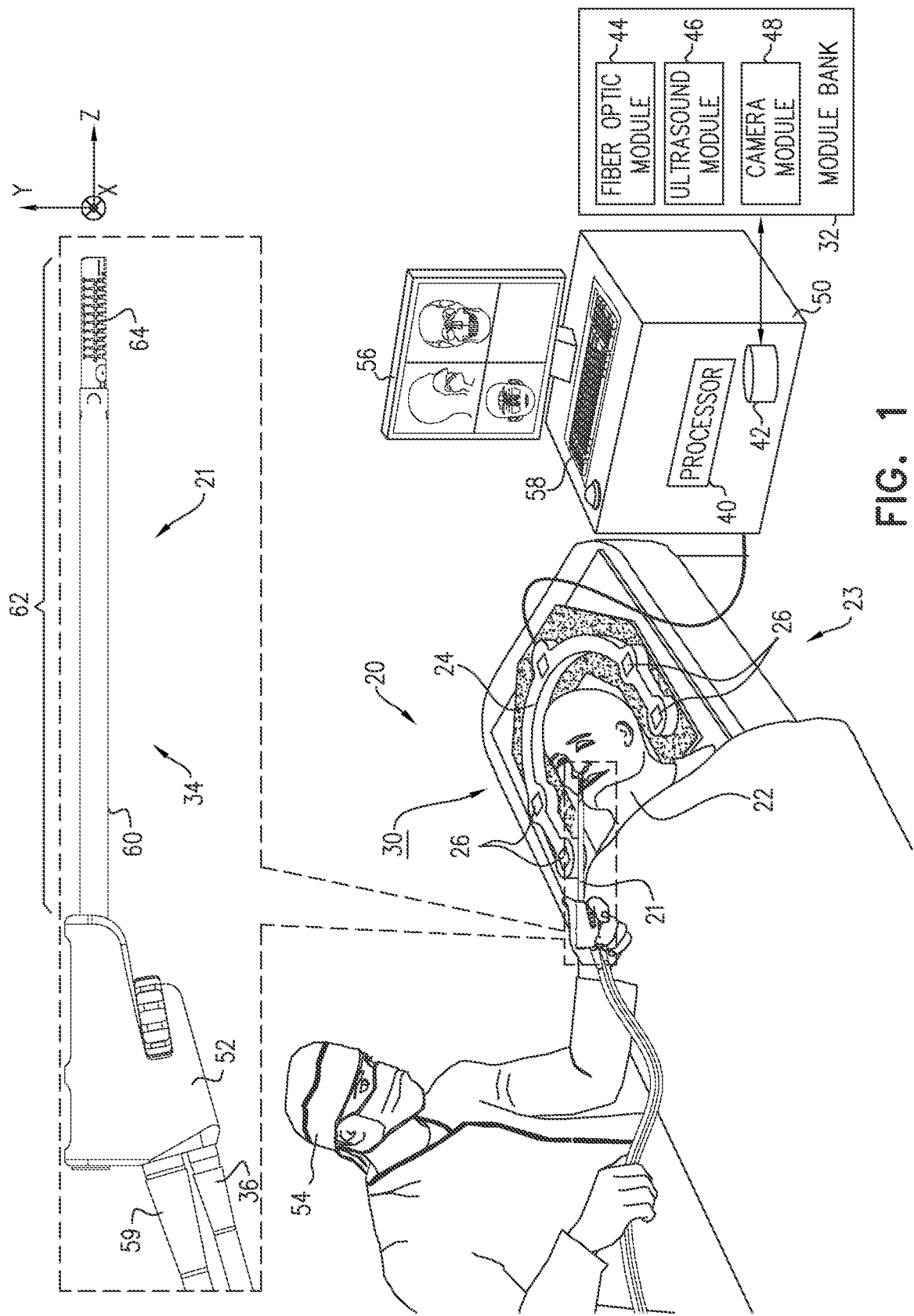
FIG. 1 is a schematic illustration of an ENT (ear, nose, and throat) system, according to an embodiment of the present invention.

Reference is now made to FIG. 1, which is a schematic illustration of an ENT (ear, nose, and throat) system 20, according to an embodiment of the present invention. In the following description system 20 is assumed to be used to perform a sinuplasty and other procedures on a patient 22, and a sinuplasty tool 21 is used for the procedures. As is described in more detail below, tool 21 comprises magnetic sensors in its distal end, and the sensors are tracked during the procedure by a magnetic tracking system 23.

Tracking system 23 comprises a magnetic radiator assembly 24 which is positioned beneath the patient's head. Assembly 24 comprises magnetic field radiators 26 which are fixed in position and which transmit alternating sinusoidal magnetic fields into a region 30 wherein the head of patient 22 is located. By way of example, radiators 26 of assembly 24 are arranged in an approximately horseshoe shape around the head of patient 22. However, alternate configurations for the radiators of assembly 24 will be apparent to those having ordinary skill in the art, and all such configurations are assumed to be comprised within the scope of the present invention. The Carto® system produced by Biosense Webster, of 33 Technology Drive, Irvine, Calif. 92618 USA, uses a tracking system similar to that described herein for finding the location and orientation of a coil in a region irradiated by magnetic fields.

Sinuplasty tool 21 comprises a probe handle 52 which is at the proximal end of the tool, and the tool also comprises a cylindrical tube 62 extending distally from the handle. Cylindrical tube 62 is formed of a rigid tube 60 and a resilient flexible tube 64, the resilient flexible tube being attached to the distal end of the rigid tube. Flexible tube 64 is configured to deflect in a controllable manner, and the flexible tube and elements used for its deflection are described in more detail below.

In the following description, for clarity tool 21 is assumed to define a set of right-handed orthogonal xyz axes, where the z axis corresponds to the axis of symmetry of tube 62, the y axis is in a plane of symmetry of the tool (and is directed up from the tool), and the x axis is orthogonal to the plane of symmetry of the tool.

Handle 52 allows a physician 54 to manipulate the tool. Tubing 59 connects to handle 52, the tubing permitting drainage of fluid through a lumen 34 of tube 60. In addition cabling 36 is connected to handle 52, the cabling enabling power to be transferred to elements in the handle, as well as enabling signals, originating in magnetic sensors in the tool, to be conveyed from the handle.

Elements of system 20, including radiators 26, are controlled by a system processor 40. The processor is also configured to receive the signals originating in the magnetic sensors, and to process the signals to derive location and orientation values for the sensors. Processor 40 may be mounted in a console 50, which comprises operating controls 58 that typically include a keypad and/or a pointing device such as a mouse or trackball. Console 50 connects to the radiators via a cable and/or wirelessly. Physician 54 uses operating controls 58 to interact with the processor while performing the procedures described herein using system 20. While performing the procedures, the processor may present results of the procedures on a screen 56.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate magnetic radiators 26 of assembly 24, and to analyze the signals received from the magnetic sensors. As stated above the radiators transmit sinusoidal alternating magnetic fields of different frequencies into region 30, including the head of patient 22, and the fields from the radiators induce signals in the magnetic sensors. The processor analyzes the signals from the sensors to determine location and orientation coordinates for the sensors in a frame of reference defined by radiator assembly 24.

Also stored in memory 42 is a software module bank 32, comprising a fiber optic module 44, an ultrasound module 46, and a camera module 48. The functions of the modules in bank 32 are explained in detail below.

Figure 2B:
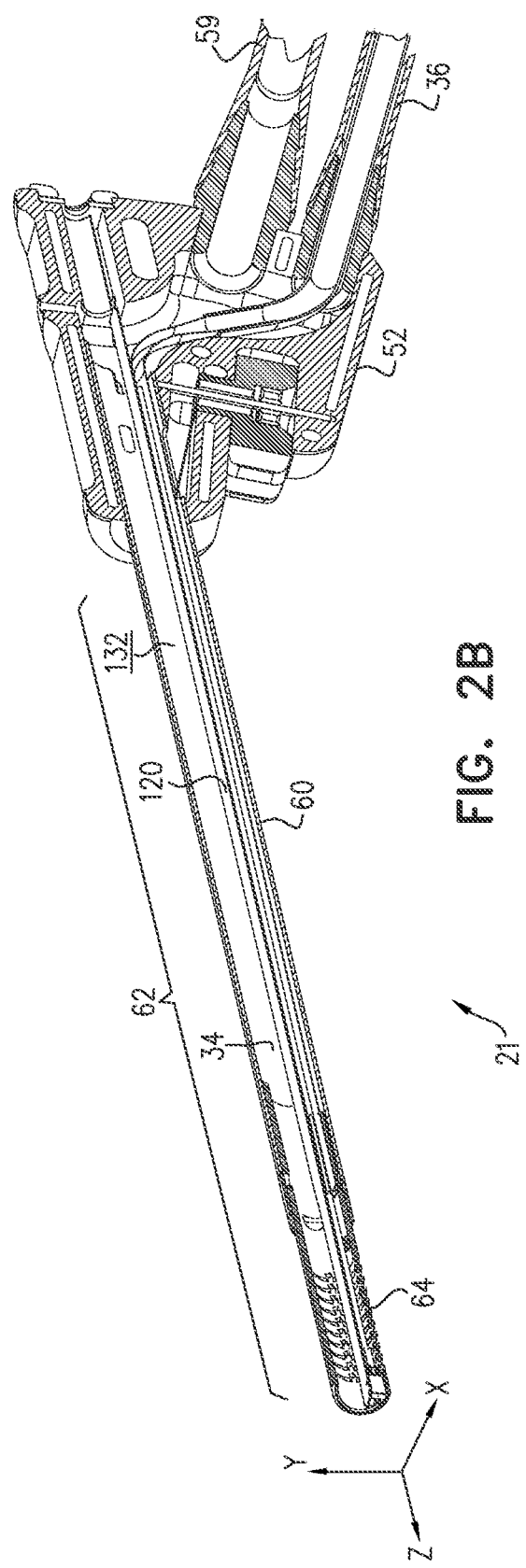
Figure 2C:
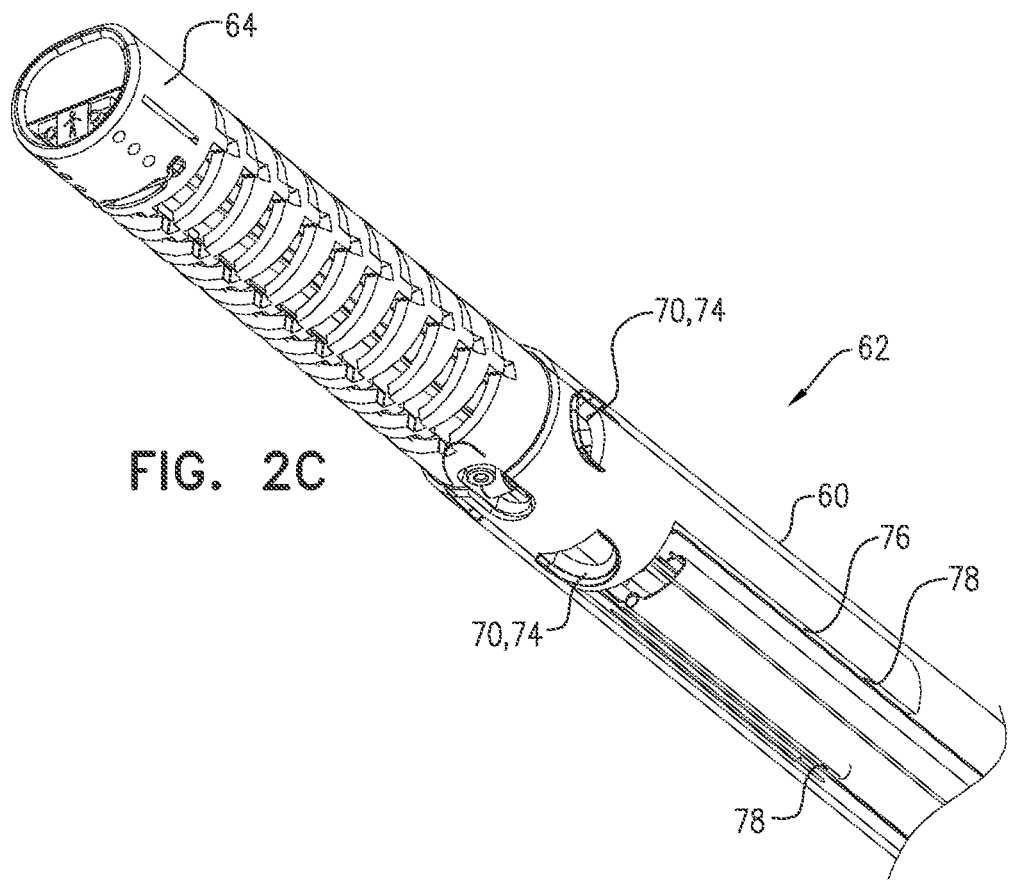
FIGS. 2C and 2D are respectively assembled and exploded views of the distal end of a cylindrical tube of the tool, according to an embodiment of the present invention.
Figure 2D:
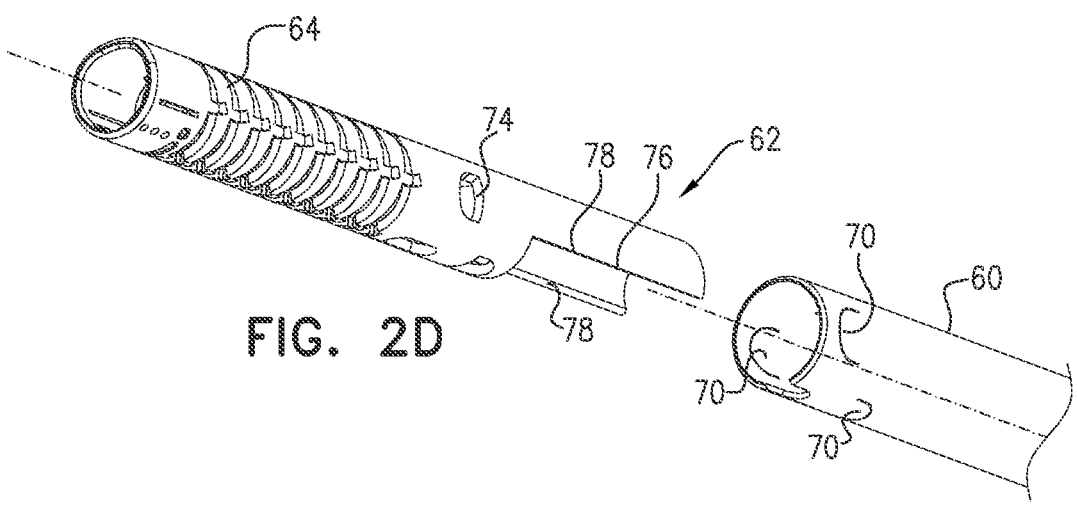

FIGS. 2A and 2B are respectively a schematic perspective figure and a schematic cut-away figure of sinuplasty tool 21, and FIGS. 2C and 2D are respectively assembled and exploded views of the distal end of cylindrical tube 62, according to an embodiment of the present invention. In a disclosed embodiment, rigid tube 60 (of cylindrical tube 62) is formed from stainless steel, while resilient flexible tube 64 (of the cylindrical tube) is typically formed from a superelastic material such as nitinol, so that tube 64 is also referred to herein as nitinol tube 64. At its distal end cylindrical tube 62 needs to be extremely flexible, so that the end can be deflected in a yz plane as illustrated in FIG. 2A.

However, making the complete tube from a sufficiently flexible material such as nitinol is expensive. To reduce the expense, while maintaining the flexibility required for the distal end, embodiments of the present invention form cylindrical tube 62 in two sections: a flexible distal tube 64, typically formed from a super-elastic material such as nitinol, and a rigid proximal tube 60, typically formed from stainless steel. In the following description rigid proximal tube 60 is also referred to as stainless steel tube 60, and flexible distal tube 64 is also referred to as nitinol tube 64.

It is difficult to connect super-elastic materials such as nitinol to stainless steel so that the connection is stable, because the materials have such dissimilar properties. For example, welding of the two materials forms intermetallic alloys in the weld, so that the welded joint is brittle and easily broken. Embodiments of the invention overcome this problem by forming spring clips 70 (FIG. 2C, 2D) in proximal stainless steel tube 60, and forming corresponding openings 74 in distal nitinol tube 64. Clips 70 are formed by laser cutting the stainless steel, and then deforming the cut sections. Nitinol tube 64 is configured to have an external diameter equal to the internal diameter of stainless steel tube 60. In one embodiment the external diameter of the nitinol tube is 4.25 mm, with an internal diameter of 3.4 mm. In this case the stainless steel tube has an external diameter of 4.8 mm and an internal diameter of 4.25 mm. In an alternative embodiment the external diameter of the nitinol tube is 3.5 mm, with an internal diameter of 3.1 mm. In this case the stainless steel tube has an external diameter of 4 mm and an internal diameter of 3.5 mm.

In production of tool 21, nitinol tube 64 is inserted into stainless steel tube 60 until clips 70 mechanically mate with their respective openings 74.

In nitinol tube 64 there is also a cutout 76 at the proximal end of the tube, the cutout providing two plane surfaces 78 in the wall of the tube. The function of plane surfaces 78 is to act as a guide for a nitinol strip 120 (FIG. 3E) described further below.

Figure 3A:
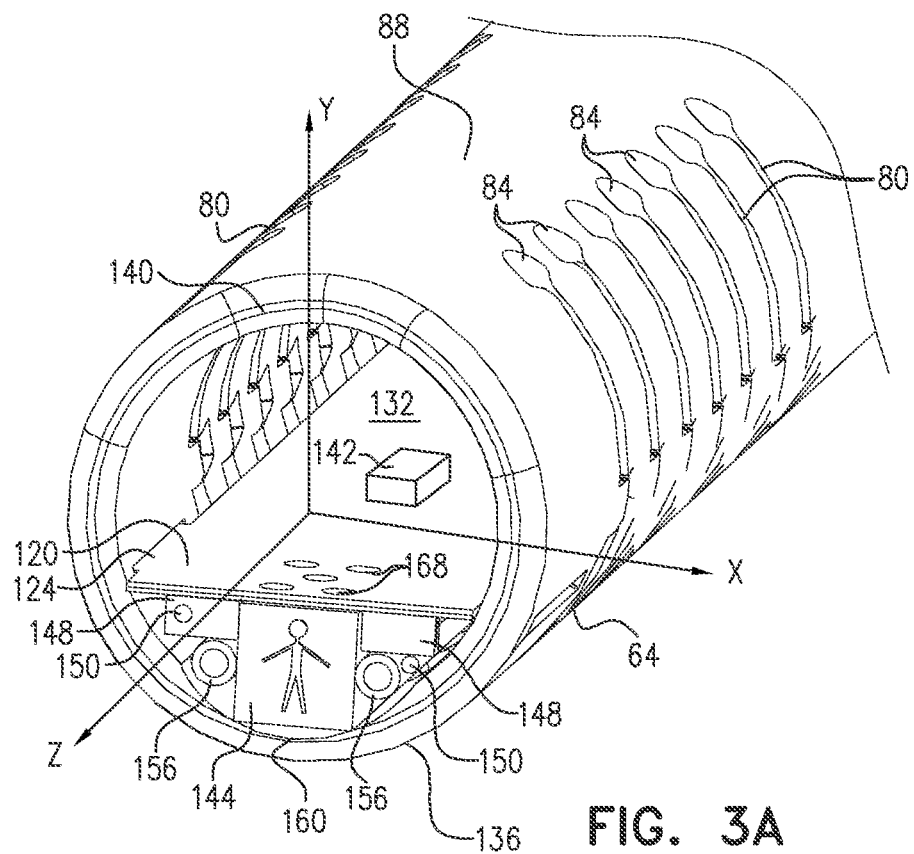
FIGS. 3A, 3B, 3C, 3D and 3E are schematic diagrams of a nitinol tube, according to an embodiment of the present invention.
Figure 3B:
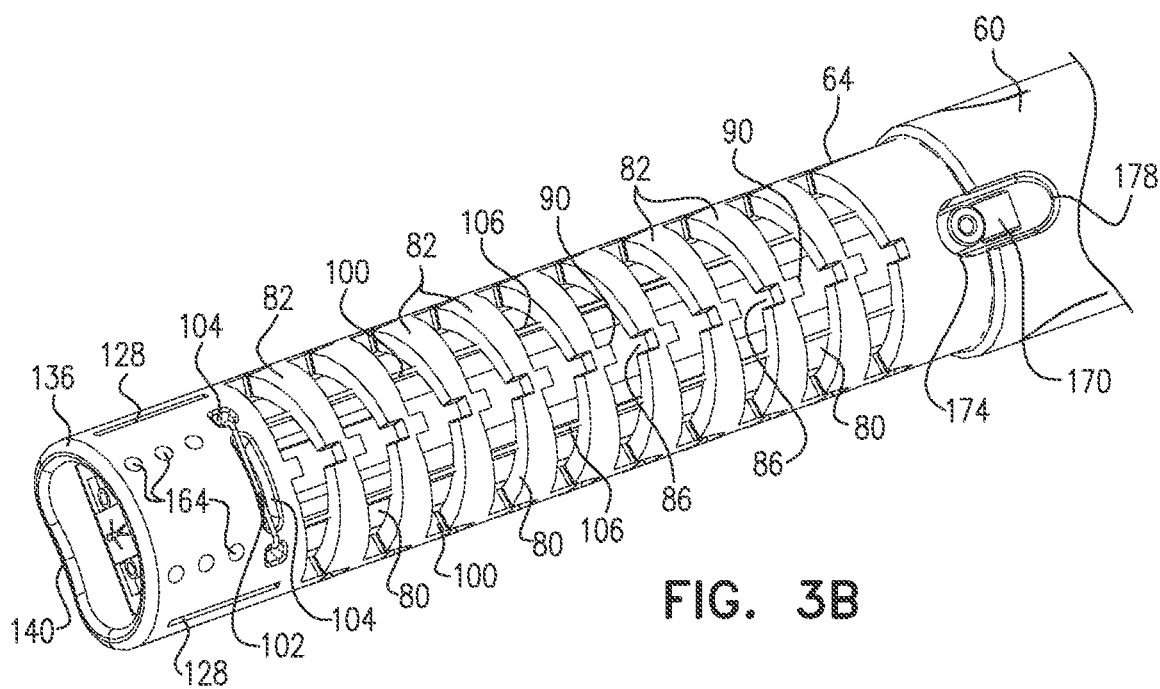
Figure 3C:
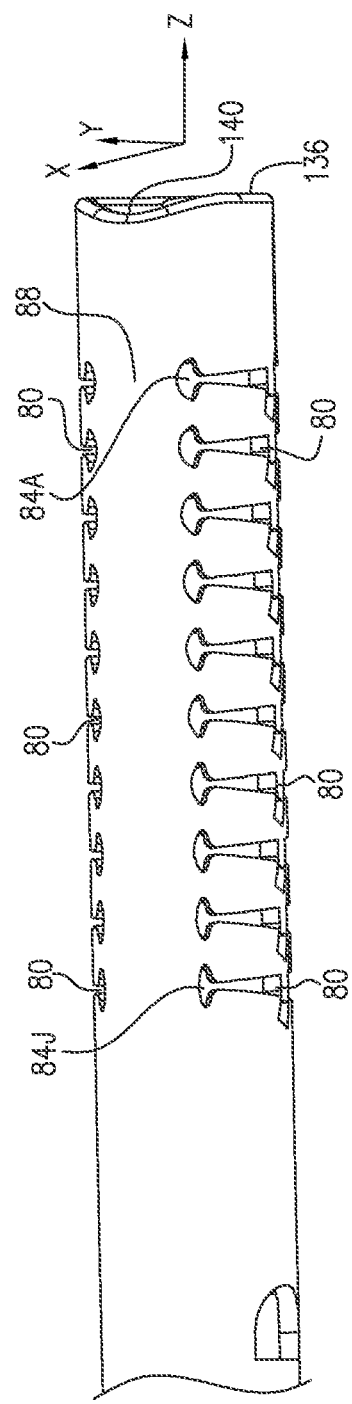
Figure 3D:
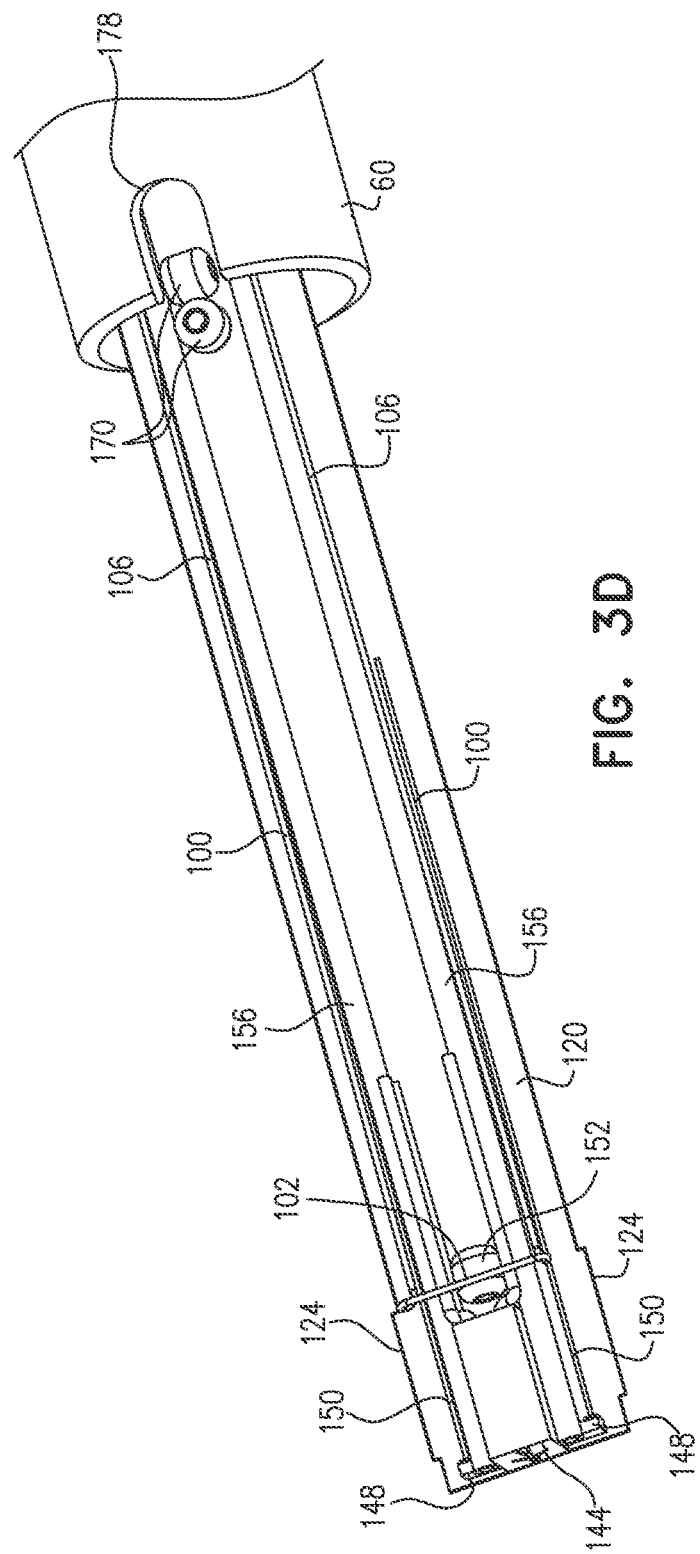
Figure 3E:
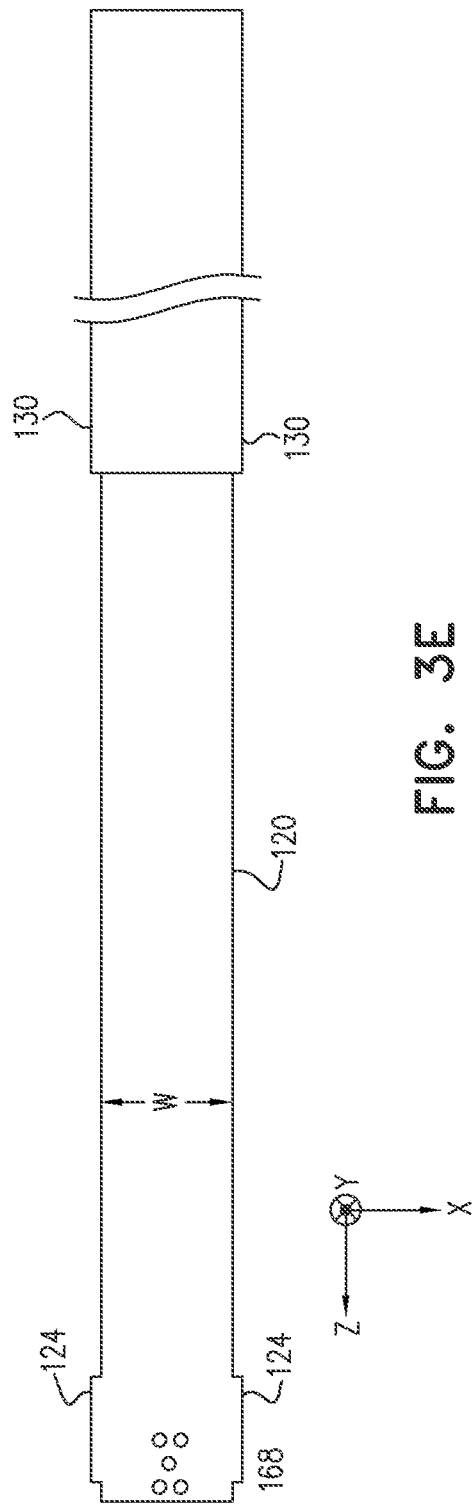

FIGS. 3A, 3B, 3C, 3D and 3E are schematic diagrams of nitinol tube 64, according to an embodiment of the present invention. FIG. 3A illustrates the distal tip of tube 64, FIG. 3B is a view of tube 64 from below the tube, FIG. 3C is a view of the tube from its side, and FIG. 3D is a view of elements internal to the tube, viewed from below the tube, and with the tube hidden. FIG. 3E is a view of nitinol strip 120, the strip being internal to the tube.

As stated above, nitinol tube 64 is deflectable in a controllable manner, and to implement the deflection a multiplicity of openings 80 are formed, typically by laser cutting, in the lower part of the tube. The openings are separated by nitinol ribs 82. Each opening 80 terminates in a pair of substantially similar approximately elliptical apertures 84A, . . . 84J, herein collectively termed apertures 84 (FIG. 3C). In addition each opening is configured to enlarge as the distance from an aperture increases, up to a maximum enlargement that is equidistant from the two apertures. Openings 80 partially encircle the tube, and in one embodiment the openings, from aperture-aperture, subtend an angle of 300° at the axis of symmetry of the nitinol tube, leaving an uncut region 88 between the apertures. Region 88 is also herein termed the spine of nitinol tube 64, and it will be appreciated that spine 88 has an approximately rectangular shape with an axis of symmetry parallel to the z-axis. Openings 80 permit spine 88 to bend, and the bending is able to continue until the openings close.

In one embodiment the exposed part of nitinol tube 64, i.e., the part not enclosed by stainless steel tube 60, is 23 mm long, and the nitinol tube has an outside diameter of 3.5 mm or 4.25 mm. For the illustrated embodiment there are ten openings 80 separating nine ribs 82, and the openings permit the nitinol tube to bend by up to approximately 120° from the z-axis. When the nitinol tube is fully bent ribs 82 contact each other, and in a disclosed embodiment the ribs comprise locking elements 86, 90 which are configured to interlock with each other when the tube is fully bent. Each rib 82 comprises one locking element 86 and one locking element 90.

By way of example, locking element 86 is female and locking element 90 is male, and when nitinol tube 64 bends a female locking element 86 on a given rib 82 mates with a male locking element 90 on an adjacent rib 82, so that the ribs interlock. The interlocking of ribs 82 assists in maintaining the integrity of nitinol tube 64 when the tube is subject to forces from the side of the tube. For example, if the physician rotates tool 21 about the axis of symmetry of tube 62 while the nitinol tube is fully bent, the interlocking prevents skewing of the shape of the tube that might be caused by the bent tube meeting resistance to the rotation.

In a disclosed embodiment openings 80 have substantially the same sizes, so that the bending they permit is approximately uniform, i.e., the radius of curvature of the bent tube is approximately constant over the whole length of the nitinol tube. In another disclosed embodiment the sizes of openings 80, and of their associated apertures 84, decreases monotonically from maximum values at the distal end of the nitinol tube to minimum values at the proximal end. Thus aperture 84A is larger than aperture 84J. Such a change in dimensions leads to the radius of curvature of the bending increasing from the tube distal end to the tube proximal end. The reduced radius of curvature at the distal end facilitates entry of the nitinol tube into narrow sinus spaces that may be present in patient 22.

A single wire 100 is threaded through preset cuts in the distal end of nitinol tube 64, so as to form a loop of wire 102 at the distal end (FIG. 3D). When tool 21 is assembled, loop 102 is cemented to tube 64 with biocompatible cement applied to wire 100 at cuts 104 (FIG. 3B). Ends 106 of the wire exiting from the loop are connected to a control wheel (FIG. 4) which, as explained below, may be operated by physician 54 so as to apply tension to the pair of wire ends. Tensioning the pair of wire ends 106, also herein termed pair 106 of wires, bends spine 88, so that nitinol tube 64 bends in a yz plane defined by the unbent spine, and the bent spine exerts a countervailing force on the pair of wires thereby maintaining the tension in the wire pair. Using a pair of wires, distributed symmetrically with respect to spine 88, prevents spine 88 from bending outside the yz plane defined by the unbent spine.

The physician may also use the control wheel to release the tension in pair 106, so that the countervailing force provided by spine 88 returns the spine to a straight configuration.

The force that spine 88 is able to apply in opposition to that of wire pair 106 depends on the thickness of the spine; the larger the thickness, the greater the force that spine 88 is able to apply. To keep the outer diameter of tube 64 as small as possible, while having a working channel as large as possible, embodiments of the present invention use a nitinol tube having an outer diameter of 3.5 mm and a wall thickness of 0.5 mm. Thus spine 88 has a thickness of approximately 0.5 mm. However, the inventors have found that because of friction there is not enough countervailing force for returning bent tube 64 to its straight configuration.

In order to provide sufficient countervailing force, an embodiment of the invention incorporates, within tube 62, an approximately rectangular resilient strip 120, typically of a super-elastic material such as nitinol, that is in an xz plane and that, as for spine 88, has an axis of symmetry parallel to the spine axis of symmetry. I.e., the strip axis of symmetry is also parallel to the z-axis. (Strip 120 is also illustrated in FIG. 2B.) Strip 120 comprises two "ears" 124 at the distal end of the strip, and the ears are configured to fit into corresponding slots 128 in tube 64. Slots 128 are shown in FIG. 3B. Strip 120 also comprises two width extensions 130, the function of which is explained below.

In one embodiment strip 120 has dimensions of length 143 mm, thickness 0.05-0.08 mm, and a width w 3 mm, the width being less than the internal diameter of nitinol tube 64, which is 3.4 mm or 3.1 mm. Strip 120 is positioned within tube 64 so that the strip edges contact the internal surface of the tube, and so that ears 124 fit into slots 128. This positioning allows strip 120 to act as a smooth lower border of a working channel 132 that is configured along all of tube 62. Thus, in addition to providing the countervailing force described above, strip 120 also acts as a smooth lower bound for working channel 132. (Spine 88 acts as a smooth upper bound of the working channel, the smoothness of the bounds preventing damage to a sinuplasty balloon traversing the channel.) Furthermore, since the width of strip 120 is less than the nitinol tube internal diameter, strip 120 may be located below the axis of symmetry of the tube, thus enhancing the size of the working channel.

During assembly of tool 21, strip 120 is inserted into tube 62, so that ears 124 fit into slots 128. Biocompatible cement is then applied to the ears and slots to fix the strip in place. The cement fixes the strip to the distal end of nitinol tube 64, but the strip is intentionally permitted to move with respect to the tube in proximal regions of the nitinol tube, as well as in proximal regions of tube 62.

It will be understood that since strip 120 is positioned below the center line of nitinol tube 64, when the tube bends downward the arc in which the strip now lies reduces in size (compared to the straight length of the unbent tube). Permitting proximal portions of the strip to move with respect to the nitinol tube allows the reduction in size to be accommodated for by the strip moving back proximally in tube 64 and tube 62. When strip 120 moves back, i.e., when nitinol tube 64 bends, width extensions 130 travel on plane surfaces 78, which act to guide the motion of the strip.

Working channel 132 terminates at a distal edge 136 of nitinol tube 64. Except as described hereinbelow, distal edge 136 is circular and lies in an xy plane. Working channel 132 is used to transport and position a sinuplasty balloon in the sinuses of patient 22 for the sinuplasty procedure referred to above. To facilitate the return of the balloon after the procedure, a recess 140 is formed in the top of edge 136, i.e., in the section of the edge opposite to strip 120. Typically, the size of the recess is determined by the size of the balloon that is to be used in the sinuplasty procedure. In one embodiment the recess has a size of 2 mm.

In some embodiments, an ultrasonic imaging camera 142 is transferred to the distal end of tube 64 along working channel 132. Alternatively, typically if installed within nitinol tube 64, ultrasonic imaging camera 142 may be fixed to the distal end of the nitinol tube, although this may reduce the size of the working channel.

Below strip 120 are an optical camera 144, a magnetic single axis sensor (SAS) 152, and irrigation tubes 156. SAS 152 may be formed as a coil, or alternatively it may be formed on a flexible PCB (printed circuit board). Camera 144 is positioned on a machined cut 160 in the base of nitinol tube 64, the machined cut allowing the camera, and thus strip 120, to be located lower within the nitinol tube. To provide illumination for the camera, embodiments of the invention comprise light emitting diodes (LEDs) 148 and/or fiber optics 150. Typically, because the space available is usually restricted, only LEDs 148 or fiber optics 150 are used.

On assembly of tool 21 camera 144, LEDs 148 and/or fiber optics 150, SAS 152, and the distal portions of tubes 156 are cemented to nitinol tube 64, at its distal end, using access holes 164 in the tube for the cement.

Once the camera, LEDs and/or fiber optics, the SAS and tubes 156 have been fixed in place, strip 120 may be positioned within the tube, using ears 124, as described above. In addition, the strip may be cemented to the camera via access holes 168 in the strip. Once strip 120 has been positioned within nitinol tube 64, a dual axis sensor (DAS) 170 may be inserted through an aperture 174, formed in nitinol tube 64, and through a mating opening 178 formed in stainless steel tube 60, and cemented to the underside of the strip. DAS 170 may be formed as coils, or alternatively it may be formed on a flexible PCB.

Figure 4:
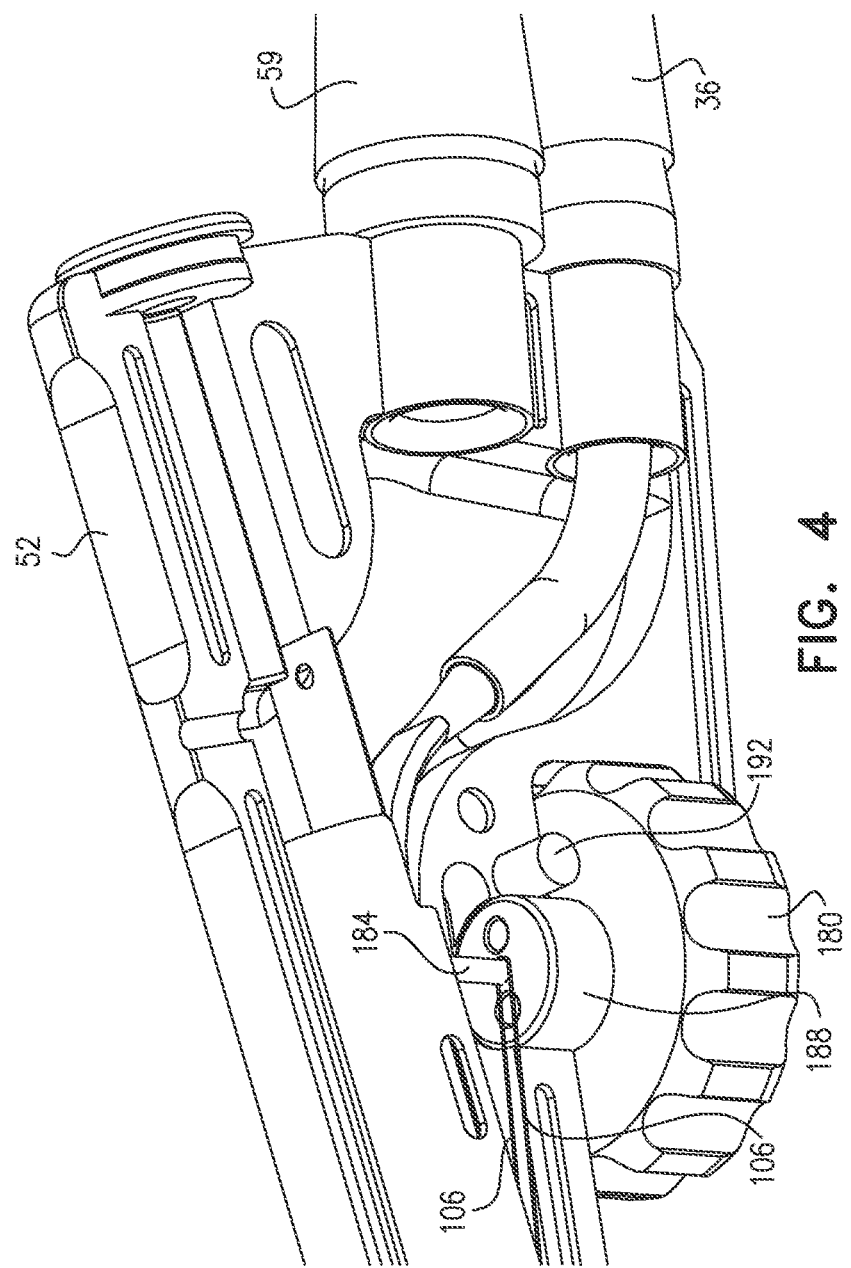
FIG. 4 is a schematic diagram of a control wheel, according to an embodiment of the present invention.

FIG. 4 is a schematic diagram of a control wheel 180, according to an embodiment of the present invention. Wheel 180, incorporated on handle 52, is fixedly attached to a central spindle 184, to which both ends 106 of wire 100 are connected. Ends 106 are attached to spindle 184 so that rotation of wheel 180 in a given direction either tautens both ends 106 of the wire or relaxes both ends of the wire.

Also fixedly attached to spindle 184 and wheel 180 is an intermediate wheel 188, and the intermediate wheel is configured to rotate against a compressible element 192 that is fixed to the body of handle 52. Element 192 acts as a brake against any rotation of spindle 184 that is not caused by rotation of wheel 180. Rotation of wheel 180 to tauten ends 106 causes nitinol tube 64 to bend from its straight shape, and the opposite rotation of the wheel, which relaxes the ends, causes the tube to return to its straight shape. In both types of rotation element 192 acts to prevent any counter-rotation, so effectively acting as an anti-backlash device for wheel 180.

Figure 5:
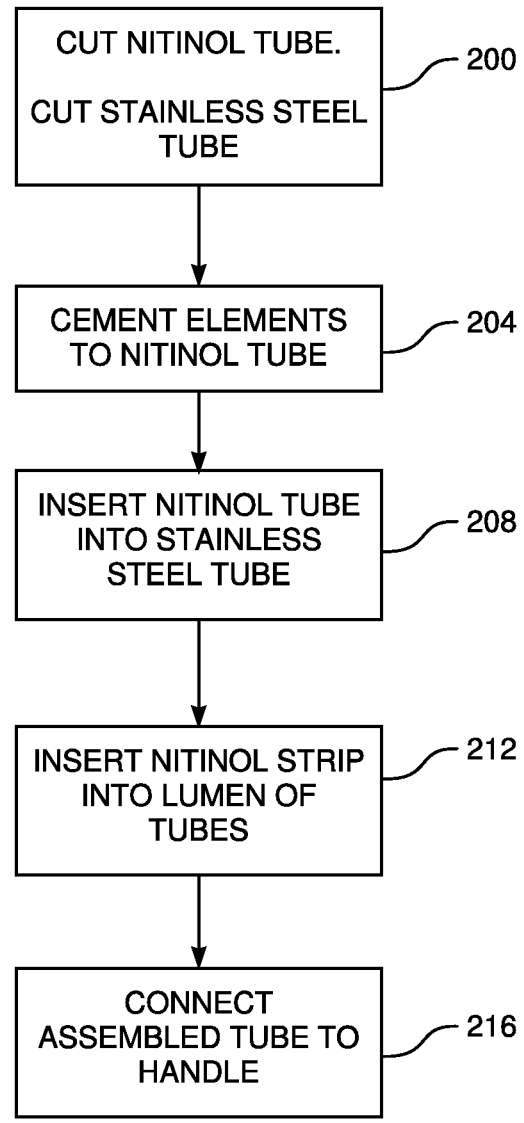
FIG. 5 is a flowchart of steps performed in assembly of a tool, according to an embodiment of the present invention.

FIG. 5 is a flowchart of steps performed in assembly of tool 21, according to an embodiment of the present invention. In a preparation step 200, tube 64 is formed by cutting openings 80, apertures 84, and ribs 82 in a cylindrical nitinol tube. In addition, access holes 164, slots 128, cuts 104, openings 74, aperture 174, and cutout 76 are also cut in the nitinol tube. Also in the preparation step, spring clips 70 and opening 178 are formed in a stainless steel tube, in order to produce stainless steel tube 60.

In an initial fixation step 204, camera 144, LEDs 148 and/or ends of fiber optics 150, ends of irrigation tubes 156, loop 102, and SAS 152 are positioned in place at the distal end of tube 64, and are cemented in place.

In an assembly step 208, cylindrical tube 62 is formed by inserting nitinol tube 64 into stainless steel tube 60, and the two tubes are cemented together so that their lumens align to form a common lumen.

In a strip introduction step 212, nitinol strip 120, which has been pre-shaped as described above with reference to FIG. 3E, is inserted into the common lumen of tube 62 until ears 124 mate with slots 128, and access holes 168 align with camera 144. The strip is then cemented in place via slots 128 and access holes 168. DAS 170 is then inserted through aperture 174 and is cemented to the underside of the strip. In a final assembly step 216, cylindrical tube 62, with nitinol strip 120 inserted, is connected to handle 52, and wires, connecting cabling, and tubing from the elements cemented to the tube are coupled to the handle.

The assembled tool may be used for the sinuplasty procedure referred to above, as well as for other procedures described below. During use of tool 21, tracking system 23 tracks the location and orientation (in three linear and three angular coordinates) of DAS 170 of the tool. The system also tracks the location and orientation (in three linear and two angular coordinates) of SAS 152, and uses the measured relationship between the two sensors to find a third angular coordinate for the SAS. By finding the complete location and orientation of SAS 152, system 23 is able to completely track the elements incorporated into the distal tip of nitinol tube 64, e.g., camera 144 and fiber optics 150 of tool 21.

Typically tracking system 23 is registered with a computerized tomography (CT) or magnetic resonance imaging (MRI) image of patient 22, which has been acquired prior to tool 21 being used on the patient. The registration may be performed by any convenient system known in the art, and it enables the location and orientation of the distal tip of the tool to be correlated with regions of the patient, such as the patient sinuses. Typically, the correlation is used to present a combined image of the distal tip of the tool incorporated into the CT or MRI image of the patient on screen 56.

In addition to tool 21 being able to perform a sinuplasty procedure, it may be used for other procedures, as described below.

Tissue Characteristic Analysis

Embodiments of the present invention comprising fiber optics 150 are configured to analyze characteristics of tissue in proximity to the distal end of nitinol tube 64, by measuring optical properties of the tissue. Fiber optics 150 are typically multi-mode fibers, and are able to transmit multiple wavelengths of light independently. In the following description, fiber optic module 44 (FIG. 1) is assumed to be configured to generate visible light, that is to be used to provide illumination for camera 144, as well as analyzing light. The analyzing light may be in the visible or near-visible spectrum, and its wavelengths are typically those having different reflectivities for diseased tissue compared to healthy tissue. In one embodiment a visible wavelength of approximately 630 nm and a near infra-red wavelength of approximately 900 nm are used.

Figure 6:
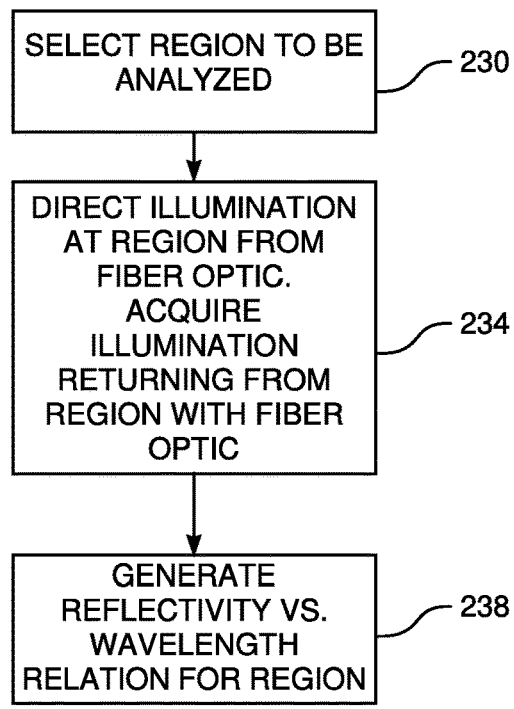
FIG. 6 is a flowchart of steps performed to analyze tissue in the sinus of a patient, according to an embodiment of the present invention.

FIG. 6 is a flowchart of steps performed by physician 54 and system 20 to analyze tissue in the sinus of patient 22, according to an embodiment of the present invention. In an initial step 230, the physician operates fiber optic module 44 to provide visible illumination, via fiber optics 150, for camera 144. The physician then navigates the distal tip of tool 21 in the patient sinus until a region of interest appears in the image of the sinus formed by the camera.

In a data acquisition step 234, the physician operates fiber optic module 44 to transmit analyzing illumination via fiber optics 150 to the region of interest. It will be understood the fiber optics 150 may transfer the visible illumination referred to above, and the analyzing illumination, independently, and that there is no interference between the two types of illumination. The fiber optics receive the analyzing illumination reflected from the tissue in the region of interest, and transfer the received illumination back to the fiber optic module.

In a final analysis step 238, system processor 40 and fiber optic module 44 use the received illumination to compute reflectivities for the region of interest at the different wavelengths of the analyzing illumination. From the computed reflectivities, the processor is able to characterize the region of interest as comprising healthy or diseased tissue, and to provide an indication of the characteristic of the tissue to physician 54 on screen 56. In one embodiment diseased tissue comprises tissue having intra-sinus inflammation. Reflectivities and wavelengths are specific to tissue type and may be found without undue experimentation.

Enhanced Image Presentation

Embodiments of the present invention use ultrasound module 46 and ultrasonic imaging camera 142 to produce a three-dimensional (3D) image of a region of interest. As is known in the art, an ultrasonic 3D image of a biological region has structure, generated by the different speeds of sound in different sections of the region being imaged. The ultrasonic 3D image may be registered with an optical image of the surface of the region of interest, so as to provide an enhanced image of the region of interest. In the following description, ultrasonic camera 142 is assumed to be introduced into the distal end of the working channel of tool 21, when physician 54 requires a 3D image of a region of interest.

Figure 7:
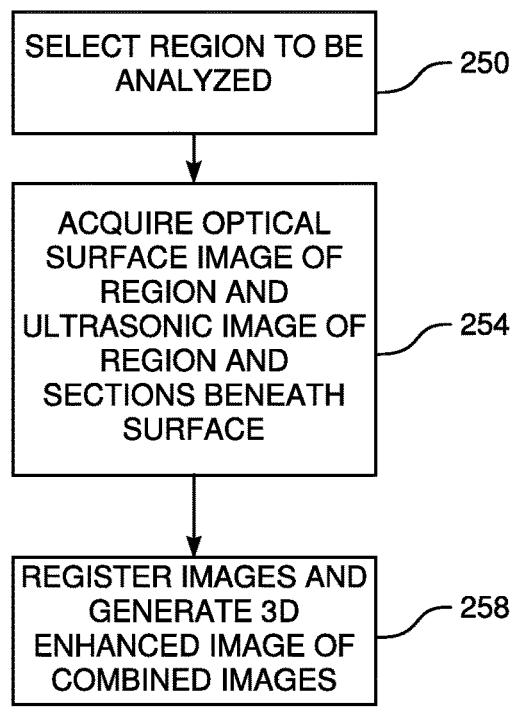
FIG. 7 is a flowchart of steps performed by to generate an enhanced image, according to an embodiment of the present invention.

FIG. 7 is a flowchart of steps performed by physician 54 and system 20 to generate an enhanced image, according to an embodiment of the present invention. In an initial step 250, the physician navigates the distal tip of tool 21 in the patient sinus until a region of interest appears in the image of the sinus formed by camera 144.

In an image acquisition step 254, the physician inserts ultrasonic camera 142 along the working channel of tool 21, to the distal tip of the tool. The physician then operates ultrasound module 46 and ultrasonic imaging camera 142 to acquire a 3D image of the region of interest. In one embodiment the camera is inserted so as to contact the tissue being imaged. In an alternative embodiment an impedance matching device such as a fluid filled balloon is placed between the camera and the tissue.

As explained above, the 3D image has structure, corresponding to different biological properties of the region being imaged. In addition, the physician acquires an optical image, using camera 144, of the surface of the region of interest.

In a final image production step 258, system processor 40 registers the surface optical image with the 3D ultrasonic image, to form a combined image showing the surface of the region of interest as well as structure beneath the surface. The processor may present the combined image to the physician on screen 56. In some cases the combined image may be further registered with a pre-acquired CT image of the patient, and incorporated into an enhanced CT image that is presented on screen 56.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An instrument, comprising:
   (a) a handle;
   (b) a rigid tube, containing a rigid tube lumen, having a rigid tube distal end and a rigid tube proximal end connected to the handle;
   (c) a resilient tube, containing a resilient tube lumen, having a resilient tube distal end and a resilient tube proximal end fixedly attached to the rigid tube distal end so that the resilient tube lumen and the rigid tube lumen align, the resilient tube having a multiplicity of separated openings partially encircling the resilient tube so as to form ribs in the resilient tube and permitting the resilient tube to bend, the resilient tube distal end being configured to be inserted into a sinus of a body of a living subject;

(d) a strip within the resilient tube lumen and configured to partition a first portion of the resilient tube lumen from a second portion of the resilient tube lumen, and (e) a wire, traversing the aligned lumens, connected to a region in proximity to the resilient tube distal end and coupled to the handle, so that applying tension to the wire causes the resilient tube to bend.

2. The instrument according to claim 1, and comprising locking elements, formed on the ribs, configured to interlock the ribs when the resilient tube is fully bent.

3. The instrument according to claim 1, the strip being fixed to the resilient tube distal end and traversing the aligned lumens.

4. The instrument according to claim 3, the wire being looped at, and connected to, a distal end of the strip, the wire having ends connected to a control in the handle.

5. The instrument according to claim 4, the control being configured to apply the tension to the wire so as bend the tube, and to release the tension so that the tube returns to an unbent shape.

6. The instrument according to claim 1, and comprising a recess formed in the resilient tube distal end, the recess being formed to facilitate return of a sinuplasty balloon to the tube.

7. The instrument according to claim 6, a size of the recess being set in response to a size of the balloon.

8. The instrument according to claim 1, and comprising at least one of a camera, an ultrasound camera, and a fiber optic located in proximity to the resilient tube distal end.

9. The instrument according to claim 1, the first portion of the resilient tube lumen forming a working channel configured to accept a portion of a surgical tool.

10. The instrument according to claim 9, further comprising an imaging device positioned in the second portion of the resilient tube lumen.

11. The instrument according to claim 10, further comprising at least one illumination source, the at least one illumination source being positioned laterally relative to the imaging device within the second portion of the resilient tube lumen.

12. The instrument according to claim 10, further comprising at least one irrigation port, the at least one irrigation port being positioned laterally relative to the imaging device within the second portion of the resilient tube lumen.

13. The instrument according to claim 1, the strip further comprising at least one protrusion projecting transversely from a distal region of the strip.

14. An instrument, comprising:
(a) a rigid tube having a rigid tube distal end and a rigid tube proximal end, the rigid tube containing a rigid tube lumen;
(b) spring retaining clips formed in the rigid tube;
(c) a resilient tube having a resilient tube distal end and a resilient tube proximal end, the resilient tube distal end being configured to be inserted into an orifice of a body of a living subject, the resilient tube containing a resilient tube lumen;
(d) apertures, cut in the resilient tube, configured to mate with the spring retaining clips so that when the apertures and the clips are mated the resilient tube proximal end fixedly attaches to the rigid tube distal end so that the rigid tube lumen and the resilient tube lumen align;
(e) a resilient strip inserted into the aligned lumens so that a resilient strip distal end aligns with the resilient tube distal end, and so that the resilient strip distal end is fixedly attached to the resilient tube distal end; and
(f) an instrument handle connected to the rigid tube proximal end.

15. The instrument according to claim 14, and comprising a multiplicity of openings partially encircling the resilient tube so as to form separating ribs in the resilient tube, the openings permitting the resilient tube to bend.

16. The instrument according to claim 15, and comprising locking elements formed on the ribs, the locking elements being configured to interlock the ribs when the resilient tube is fully bent.

17. The instrument according to claim 15, and comprising a wire, looped at the distal end of the resilient strip, having ends of the wire connected to a control in the instrument handle.

18. The instrument according to claim 17, and comprising using the control to apply the tension to the wire so as bend the resilient tube, and to release the tension so that the resilient tube returns to an unbent shape.

19. The instrument according to claim 14, and comprising at least one of a camera, an ultrasound camera, and a fiber optic located in proximity to the resilient tube distal end.

20. A surgical instrument, comprising:
(a) a handle;
(b) a rigid tube, containing a rigid tube lumen, having a rigid tube distal end and a rigid tube proximal end connected to the handle;
(c) a resilient tube, containing a resilient tube lumen, having a resilient tube distal end and a resilient tube proximal end fixedly attached to the rigid tube distal end so that the resilient tube lumen and the rigid tube lumen align, the resilient tube having a multiplicity of separated openings partially encircling the resilient tube so as to form ribs in the resilient tube and permitting the resilient tube to bend, the resilient tube distal end being configured to be inserted into a sinus of a body of a living subject;
(d) a fluid conduit configured to provide irrigation fluid to the resilient tube distal end; and
(e) a strip within the resilient tube lumen, the strip and the resilient tube lumen collectively defining a working channel on a first side of the strip, the fluid conduit being positioned on a second side of the strip, the first and second sides of the strip being opposite one another along the strip such that the strip is laterally interposed between the working channel and the fluid conduit.

* * * * *